( 12 ) United States Patent
Luo

(10) Patent No.: US 11,450,815 B2
(45) Date of Patent: Sep. 20, 2022

(54) HOLE TRANSPORTING MATERIAL, METHOD OF MANUFACTURING SAME AND ORGANIC ELECTROLUMINESCENT DEVICE

(71) Applicant: WUHAN CHINA STAR OPTOELECTRONICS SEMICONDUCTOR DISPLAY TECHNOLOGY CO., LTD., Wuhan (CN)

(72) Inventor: Jiajia Luo, Wuhan (CN)

( * ) Notice: Subject to any disclaimer, the term of this patent is extended or adjusted under 35 U.S.C. 154(b) by 184 days.

(21) Appl. No.: 16/754,140

(22) PCT Filed: Nov. 19, 2019

(86) PCT No.: PCT/CN2019/119541
§ 371 (c)(1),
(2) Date: Apr. 7, 2020

(87) PCT Pub. No.: WO2021/027172
PCT Pub. Date: Feb. 18, 2021

(65) Prior Publication Data
US 2021/0151690 A1    May 20, 2021

(30) Foreign Application Priority Data

Aug. 13, 2019  (CN) .......................... 201910744472.0

(51) Int. Cl.
*C07D 471/18* (2006.01)
*H01L 51/50* (2006.01)
*H01L 51/00* (2006.01)
*C07C 209/74* (2006.01)
*C07D 471/16* (2006.01)

(52) U.S. Cl.
CPC ........ *H01L 51/0072* (2013.01); *C07C 209/74* (2013.01); *C07D 471/16* (2013.01); *H01L 51/0071* (2013.01); *H01L 51/5056* (2013.01)

(58) Field of Classification Search
CPC .... C07D 471/18; H01L 51/50; H01L 51/5056

USPC .................................. 544/338; 313/498, 504
See application file for complete search history.

(56) References Cited

U.S. PATENT DOCUMENTS

2015/0295186 A1    10/2015 Parham et al.

FOREIGN PATENT DOCUMENTS

| CN | 102203212 A | 9/2011 |  |
|---|---|---|---|
| CN | 104471020 A | 3/2015 |  |
| CN | 109810106 A | 5/2019 |  |
| CN | 110590790 A | * 12/2019 | ........... C07D 487/20 |
| JP | H11339868 A | 12/1999 |  |

\* cited by examiner

*Primary Examiner* — Charanjit Aulakh

(57) ABSTRACT

A hole transporting material is disclosed, and has a structural formula as shown in a formula (A):

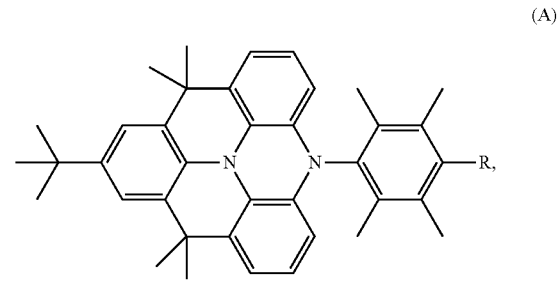

(A)

wherein R group of the hole transporting material is one of a carbazole group and a derivative group thereof, a diphenylamine group and a derivative group thereof, a phenoxazine group and a derivative group thereof, and an acridine group and a derivative group thereof. The hole transporting material is synthetized to have a suitable energy level and a high mobility by using an acridine structure as a core. An organic electroluminescent device based on the hole transporting material has high luminous efficiency.

11 Claims, 3 Drawing Sheets

HOLE TRANSPORTING MATERIAL, METHOD OF MANUFACTURING SAME AND ORGANIC ELECTROLUMINESCENT DEVICE

CROSS REFERENCE TO RELATED APPLICATIONS

The present application claims priority to Chinese Patent Application No. 201910744472.0, entitled "HOLE TRANSPORTING MATERIAL, METHOD OF MANUFACTURING SAME AND ORGANIC ELECTROLUMINESCENT DEVICE", and filed on Aug. 13, 2019, the entire disclosure of which is incorporated herein by reference.

FIELD OF INVENTION

The present disclosure relates to the technical field of displays, and in particular, to a hole transporting material, a method for manufacturing the same, and an organic electroluminescent device.

BACKGROUND OF DISCLOSURE

Organic light-emitting diodes (OLED) are greatly concerned by industries due to advantages of active light emitting, high luminous efficiency, wide viewing angles, fast response times, low driving voltages, low energy consumption, light weights, and their wide application prospects. In the OLED light-emitting material, light-emitting guest material is critical to performance thereof.

The light-emitting guest material used in the early OLEDs is fluorescent material. Since a ratio of single excitons to triplet excitons in the OLEDs is 1:3, theoretical internal quantum efficiency based on the OLEDs of fluorescent material can only reach 25%, so as to greatly limit the application thereof in fluorescent electroluminescent devices. Heavy metal complex phosphorescent material can achieve 100% theoretical internal quantum efficiency by using singlet excitons and triplet excitons simultaneously due to the spin-orbit coupling of heavy atoms. However, most of the commonly-used heavy metals are precious metals, such as iridium and platinum, and, moreover, phosphorescent heavy-metal complex material has no prominent progress yet in terms of blue light material.

For top-emitting OLED devices currently in use, hole transport layers are thicker than other film layers, and energy levels thereof and hole mobility are always in a conflicting relationship. Thus, it is urgent to develop hole-transport material with corresponding energy levels and high mobility.

SUMMARY OF INVENTION

The present disclosure provides a hole transporting material and a method of manufacturing the same and an organic electroluminescent device, to solve the problems that a highest occupied molecular orbital energy level does not match a lowest unoccupied molecular orbital energy level in the hole transporting material in existing OLED light emitting devices, and mobility of the hole transporting material is not high, thus affecting luminous efficiency of the OLED devices.

In order to solve the aforementioned problem, a technical solution provided by the present disclosure is as follows:

The present disclosure provides a hole transporting material, having a structural formula as shown in the following formula (A):

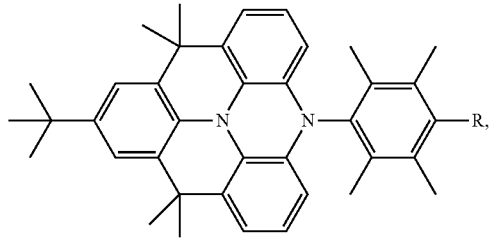

wherein R group is one of a carbazole group and a derivative group thereof, a diphenylamine group and a derivative group thereof, a phenoxazine group and a derivative group thereof, and an acridine group and a derivative group thereof.

In at least one embodiment of the disclosure, the R group is one of the following structural formula:

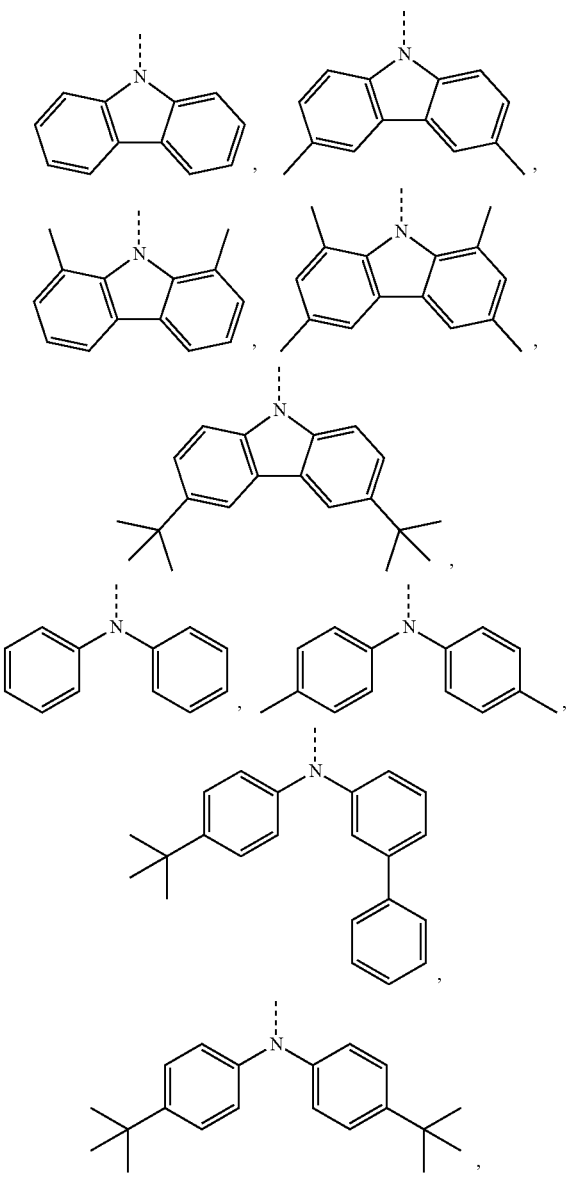

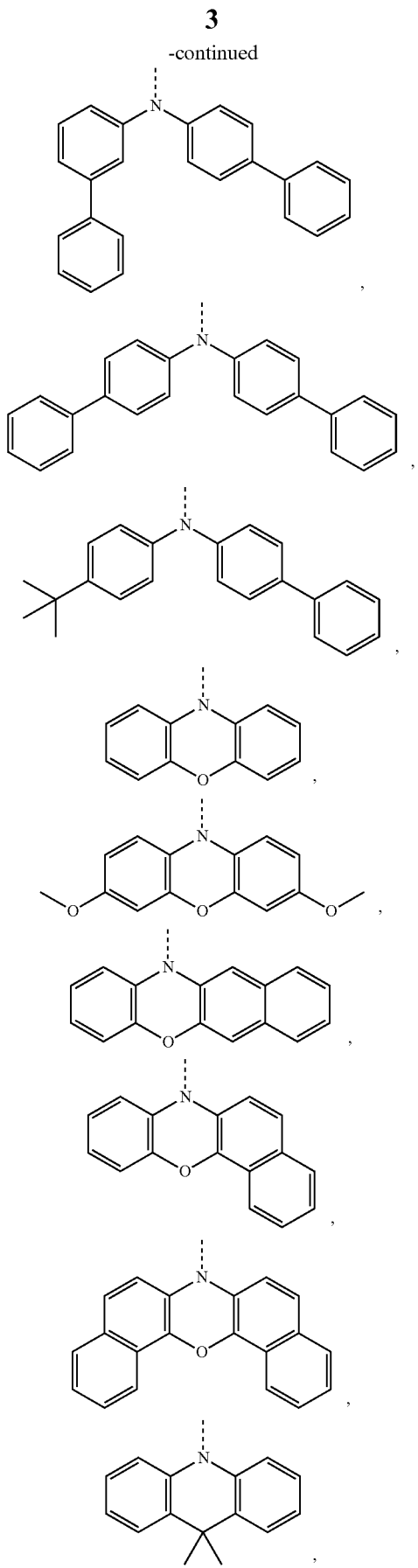
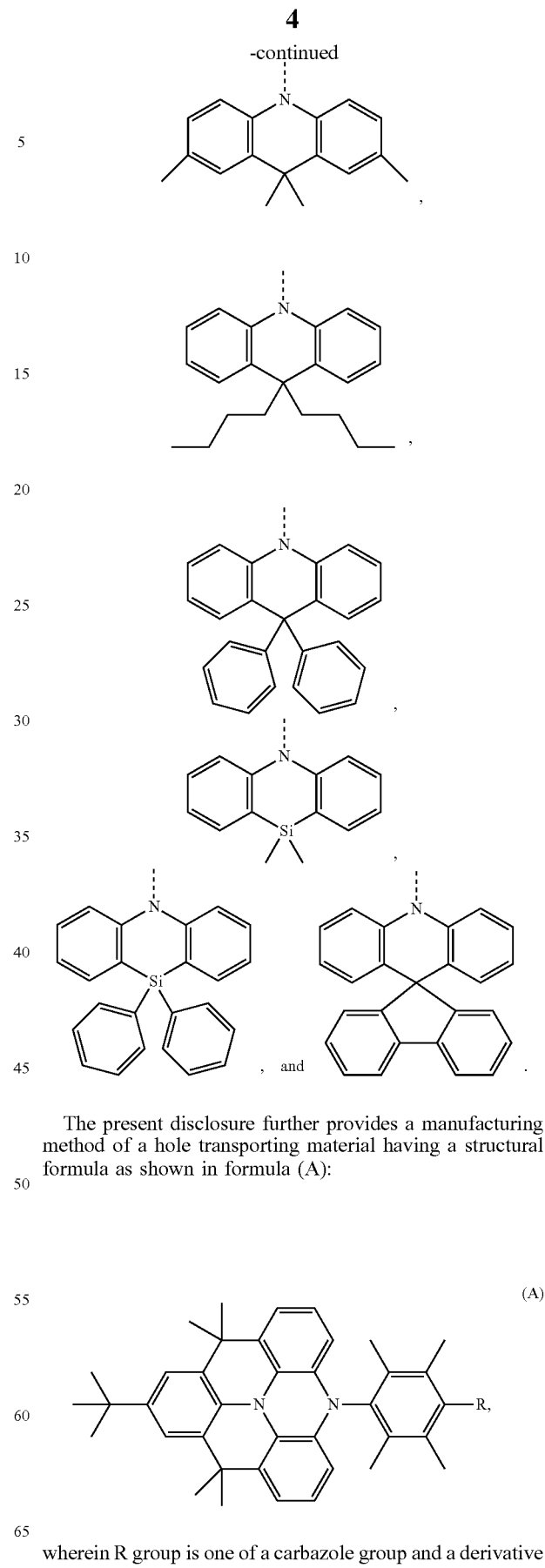
The present disclosure further provides a manufacturing method of a hole transporting material having a structural formula as shown in formula (A):
(A)
wherein R group is one of a carbazole group and a derivative group thereof, a diphenylamine group and a derivative group thereof, a phenoxazine group and a derivative group thereof, and an acridine group and a derivative group thereof, the manufacturing method of the hole transporting material comprising: a step S10 of mixing a first reactant, a second reactant, palladium acetate and tri-tert-butylphosphine tetrafluoroborate to obtain a mixed solution; a step S20 of disposing the mixed solution in a glove box, adding sodium tert-butoxide and toluene into the mixed solution to react, and cooling to room temperature to obtain a reacted solution; and a step S30 of extracting the reacted solution, combining organic phases obtained by extracting, and isolating and purifying the organic phases to obtain the hole transporting material.

In at least one embodiment of the disclosure, the second reactant is one of carbazole and derivatives thereof, diphenylamine and derivatives thereof, phenoxazine and derivatives thereof, and acridine and derivatives thereof.

In at least one embodiment of the disclosure, the second reactant is one of carbazole, phenoxazine and 9,9'-dimethylacridine.

In at least one embodiment of the disclosure, a structural formula of the first reactant is as shown in formula (B):

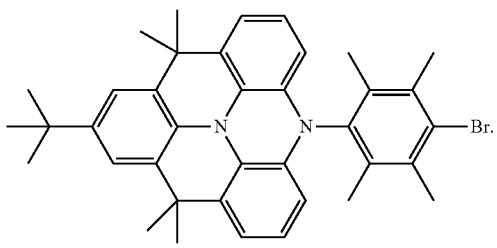

(B)

In at least one embodiment of the disclosure, the first reactant is prepared by: a step S101 of reacting 4,4'-dibromo-4'-tert-butyltriphenylamine with chloroacetyl chloride to obtain a first intermediate, wherein a structural formula of the first intermediate is as shown in formula (C):

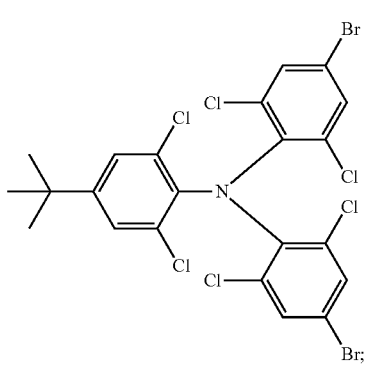

(C)

a step S102 of reacting the first intermediate with copper cyanide and ferrous chloride to obtain a second intermediate, wherein a structural formula of the second intermediate is as shown in formula (D):

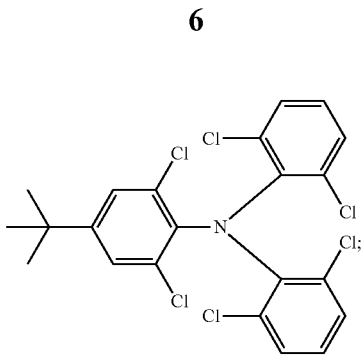

(D)

a step S103 of reacting the second intermediate with acetone to obtain a third intermediate, wherein a structural formula of the third intermediate is as shown in formula (E):

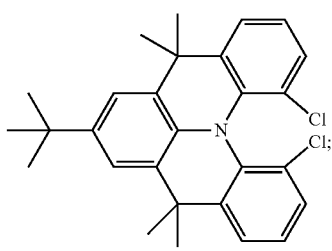

(E)

and a step S104 of reacting the third intermediate with 4-bromo-2,3,5,6-tetramethylaniline to obtain the first reactant.

In at least one embodiment of the disclosure, in the step S20, reaction temperature is 120° C. and reaction time is 24 hours.

In at least one embodiment of the disclosure, the step S30 comprises steps of: pouring the reaction solution into ice water, and combining the organic phases obtained after extracting several times with dichloromethane; and performing rotary evaporation to the organic phases to obtain silica gel, and then isolating and purifying by using column chromatography to obtain the hole transporting material.

The present disclosure further provides an organic electroluminescent device, comprising: a hole transporting material having a structural formula as shown in the following formula (A):

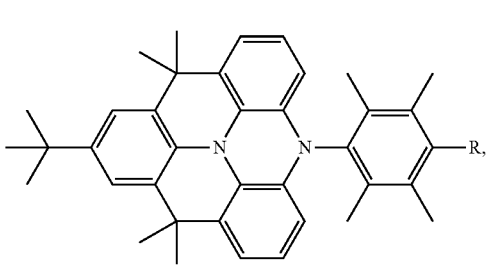

(A)

wherein R group is one of a carbazole group and a derivative group thereof, a diphenylamine group and a derivative group thereof, a phenoxazine group and a derivative group thereof, and an acridine group and a derivative group thereof.

In at least one embodiment of the disclosure, the R group is one of the following structural formulas:
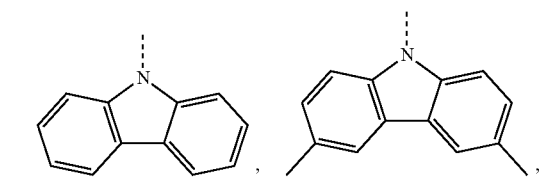,
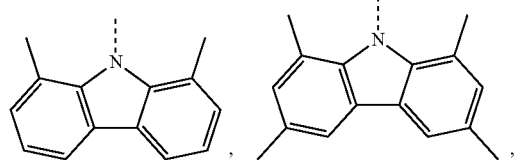,
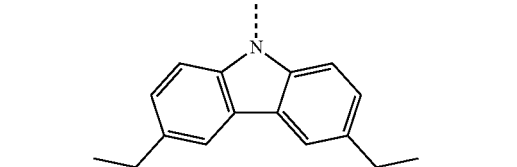,
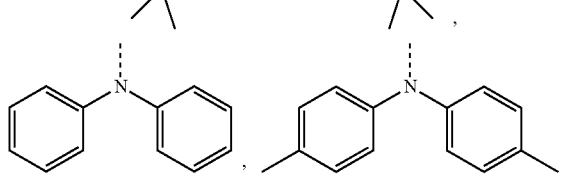,
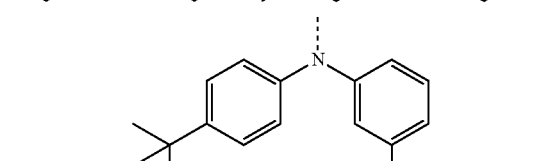,
,
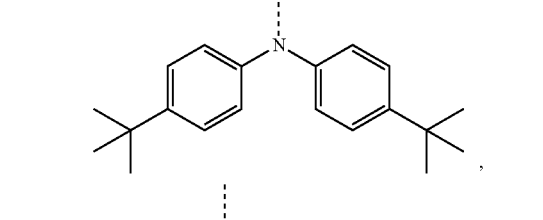,
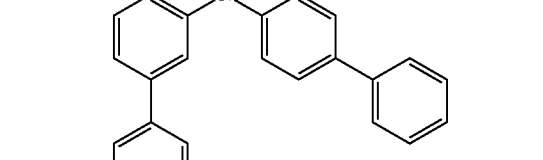,
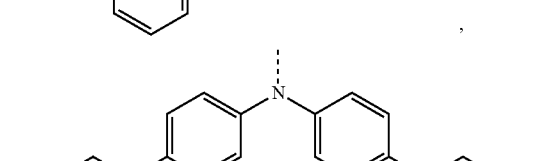,
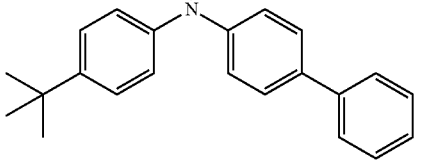,
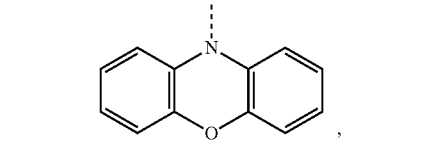,
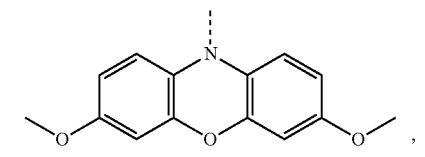,
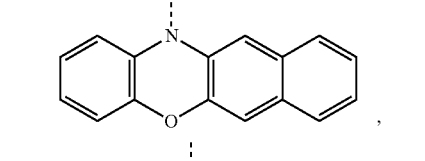,
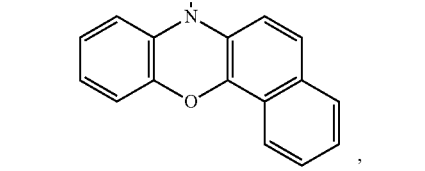,
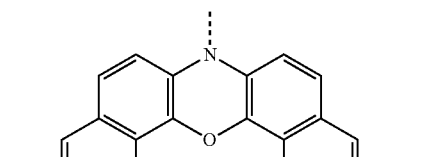,
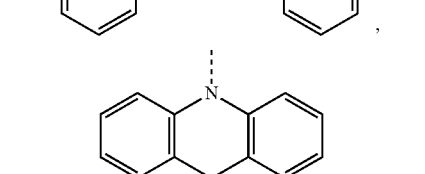,
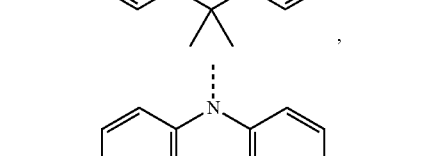,
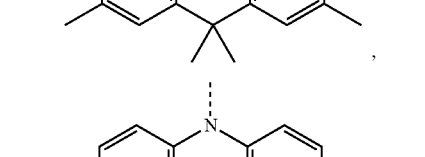,
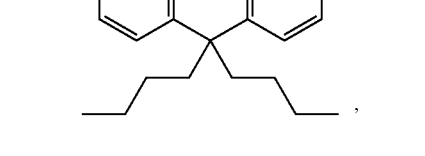,

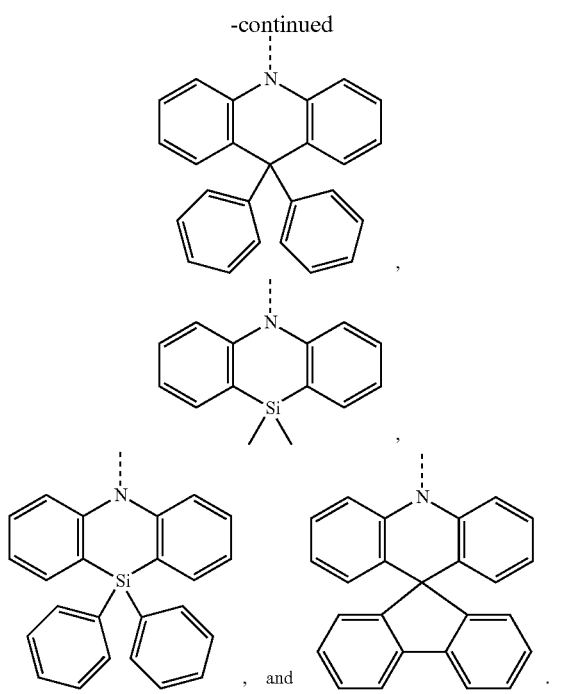
, and .

The present disclosure has the beneficial effects that the hole transporting material is synthetized to have a suitable energy level and a high mobility by using an acridine structure as a core with different functional groups, and an organic electroluminescent device based on the hole transporting material has high luminous efficiency.

BRIEF DESCRIPTION OF THE DRAWINGS

To describe the technical solutions of the embodiments or the prior art more clearly, the following outlines briefly the accompanying drawings for describing the embodiments of the present disclosure or the prior art. Apparently, the accompanying drawings described below are merely about some embodiments of the present disclosure, and persons of ordinary skill in the art can derive other drawings from the accompanying drawings without any creative effort.

DETAILED DESCRIPTION OF EMBODIMENTS

Figure 1:
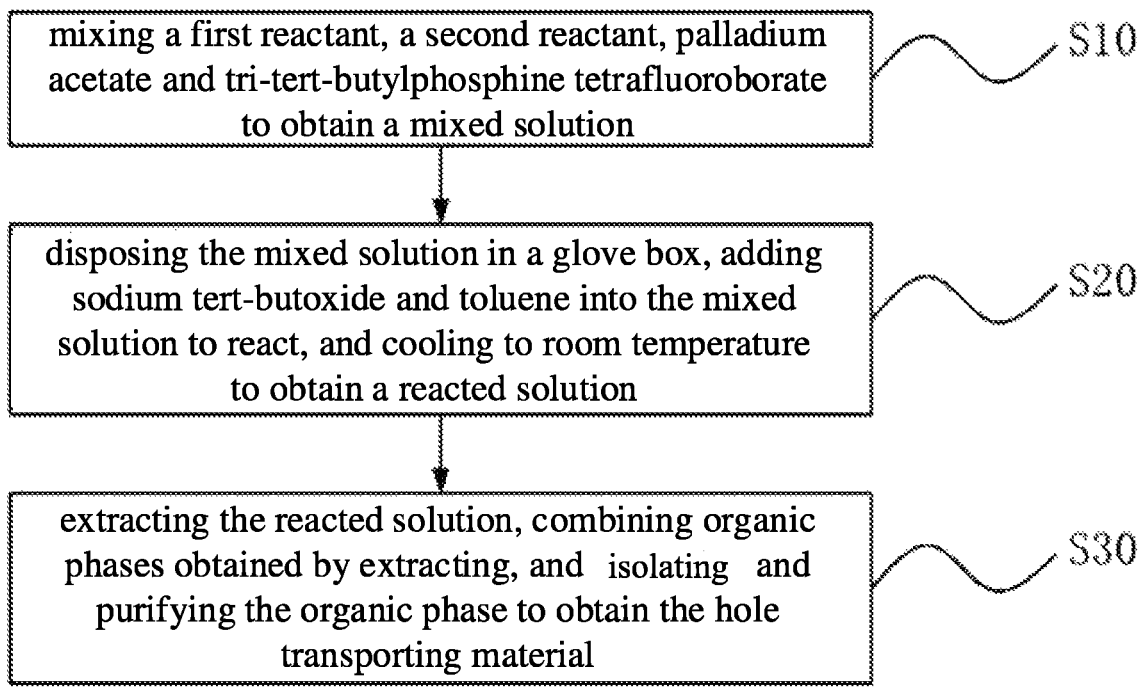
FIG. 1 is a flowchart of the manufacturing method of the hole transporting material according to the embodiment of the present disclosure.

The following embodiments are referring to the accompanying drawings for exemplifying specific implementable embodiments of the present disclosure. Furthermore, directional terms described by the present disclosure, such as "upper", "lower", "front", "back", "left", "right", "inner", "outer", "side" and etc., are only directions by referring to the accompanying drawings, and thus the used directional terms are used to describe and understand the present disclosure, but the present disclosure is not limited thereto. In the drawings, structure-like elements are labeled with like reference numerals.

The present disclosure is provided for the prior art OLED light-emitting device, which has technical problems that a highest occupied molecular orbital energy level does not match a lowest unoccupied molecular orbital energy level of the hole transporting material in existing OLED light emitting devices, and migration rate of the hole transporting material is not high, thus affecting the technical problem of luminous efficiency of the OLED devices. The present embodiments are capable of solving the defects.

An embodiment of the present disclosure provides a hole transporting material, having a structural formula as shown in the following formula (A):

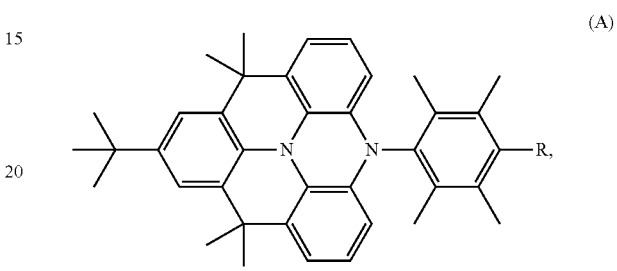

(A)

wherein R group is one of a carbazole group and a derivative group thereof, a diphenylamine group and a derivative group thereof, a phenoxazine group and a derivative group thereof, and an acridine group and a derivative group thereof.

Specifically, the carbazole group and the derivative group can be one of the following structural formulas, but are not limited to the following structural formulas:

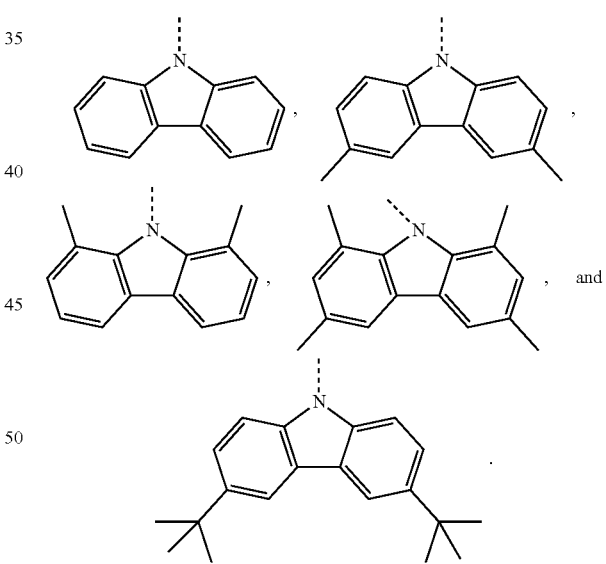

, and .

The diphenylamine group and the derivative group can be one of the following structural formulas, but are not limited to the following structural formulas:

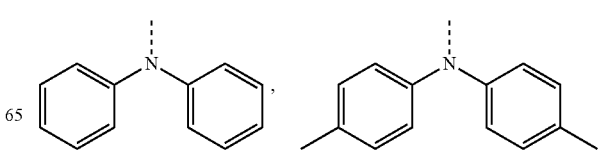

, ,

-continued
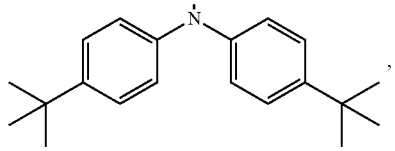,
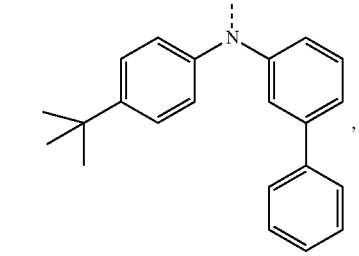,
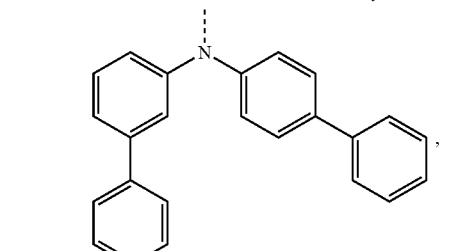,
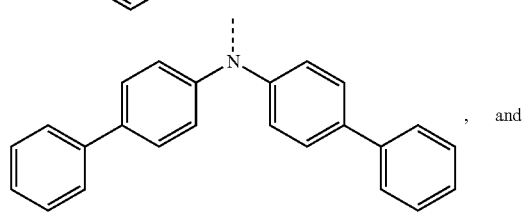, and
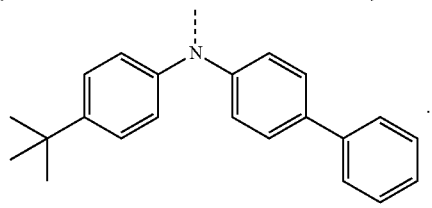.
The phenoxazine group and the derivative group can be one of the following structural formulas, but are not limited to the following structural formulas:
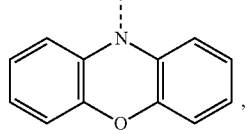,
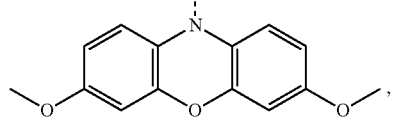,
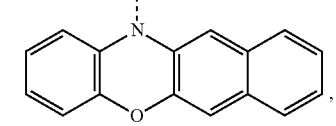,
-continued
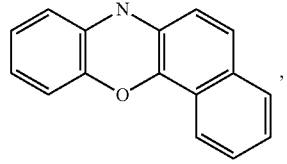, and
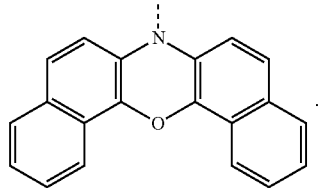.
The acridine group and the derivative group can be one of the following structural formulas, but are not limited to the following structural formulas:
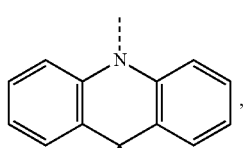, 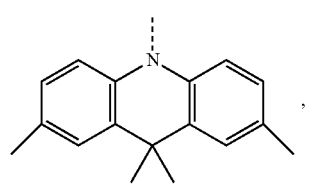,
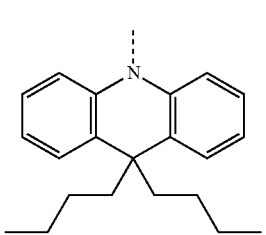, 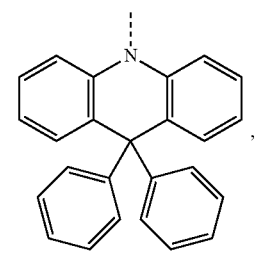,
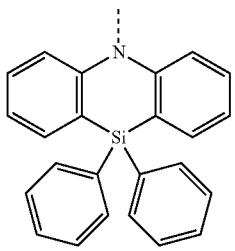, 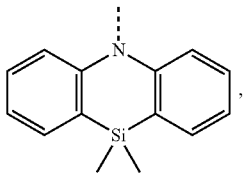,

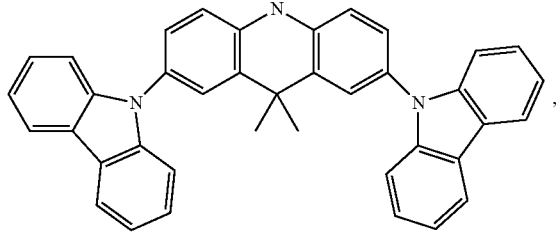,

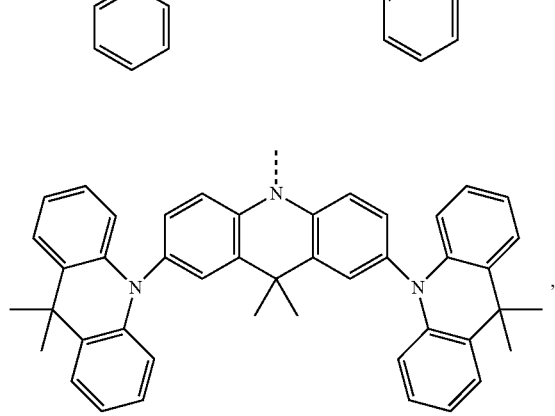,

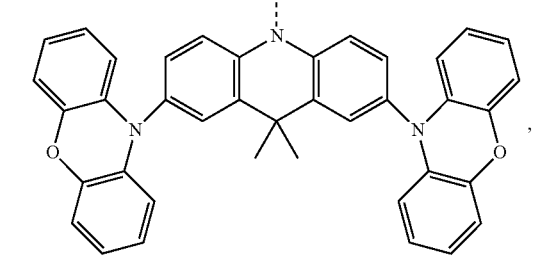,

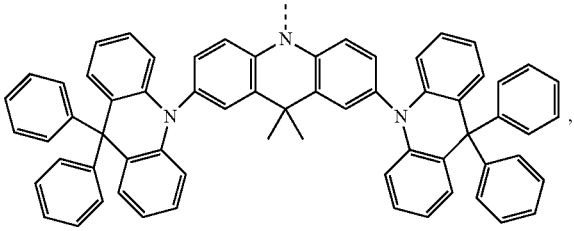,

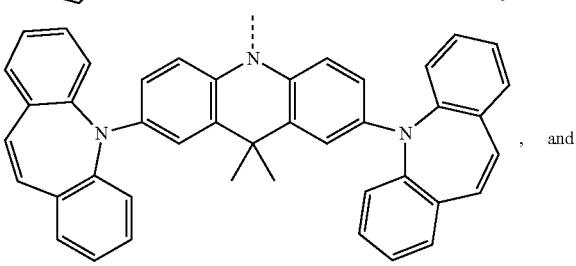 and

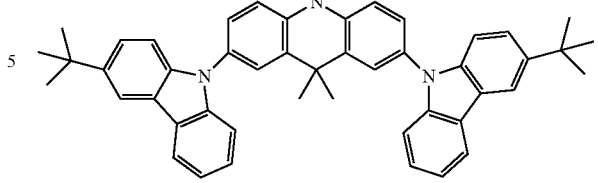

As shown in FIG. 1, the embodiment provides a method for manufacturing the above hole transporting material, which comprises the following steps:

a step S10 of mixing a first reactant, a second reactant, palladium acetate and tri-tert-butylphosphine tetrafluoroborate to obtain a mixed solution;

a step S20 of disposing the mixed solution in a glove box, adding sodium tert-butoxide and toluene into the mixed solution to react, and cooling to room temperature to obtain a reacted solution; and a step S30 of extracting the reacted solution, combining organic phases obtained by extracting, and isolating and purifying the organic phases to obtain the hole transporting material.

A structural formula of the first reactant is as shown in formula (B):

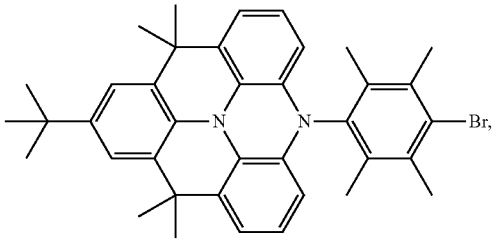

(B)

wherein the structural formula of the second reactant corresponds to the R group, and may be one of a carbazole group and a derivative group thereof, a diphenylamine group and a derivative group thereof, a phenoxazine group and a derivative group thereof, and an acridine group and a derivative group thereof.

The hole transporting material has an acridine structure as a core. Since the acridine has a strong electron donating ability, and is further coupled with other electron donating groups, the synthesized material has a high mobility. In the embodiment of the present disclosure, the structure of the synthesized hole transporting material is confirmed by mass spectrometry. The present disclosure is described in detail below by the manufacturing method of the hole transporting material.

Embodiment 1

The first reactant (3.02 g, 5 mmol), carbazole (1.00 g, 6 mmol), palladium acetate (45 mg, 0.2 mmol), and tri-tert-butylphosphine tetrafluoroborate (0.17 g, 0.6 mmol) were added into a 250 mL two-neck flask to obtain a mixed solution. Then, the mixed solution was placed in a glove box, sodium tert-butoxide (NaOt-Bu, 0.58 g, 6 mmol) was added into the mixed solution, and then in the presence of argon, 100 mL of dried and deoxidized toluene was introduced to react at 120° C. for 24 hours. A reacted solution is obtained after cooling to room temperature. The reacted solution was poured into 200 mL of ice water and extracted three times with dichloromethane. Then, organic phases were combined with the reacted solution, and rotary evaporation was performed to obtain silica gel. Isolation and purification were conducted by using column chromatography (the volume ratio of dichloromethane to n-hexane: 1:5) to obtain a target compound 1. The target compound 1 is 2.2 g of white powder and the yield is 64%. Mass spectrometry was performed on the white powder to obtain MS (EI) m/z: [M]⁺: 691.39 The theoretical relative molecular weight of the target compound 1 is 691.40.

The synthetic route for the hole transporting material is as shown in the following formula (1):

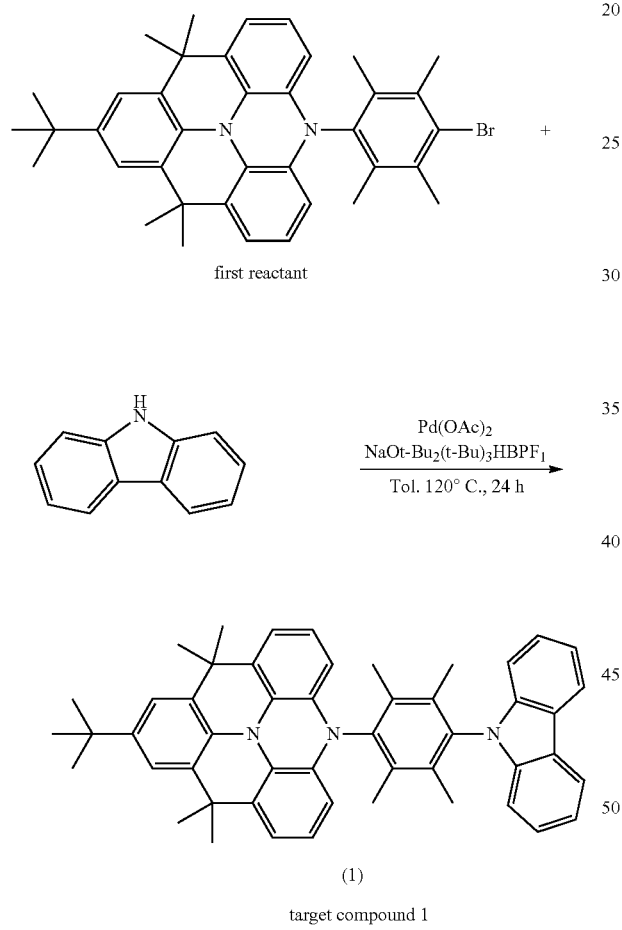

The target compound 1 has a highest occupied molecular orbital electrochemical energy level of −5.58 eV, and a lowest unoccupied molecular orbital electrochemical energy level of −2.60 eV.

Figure 2:
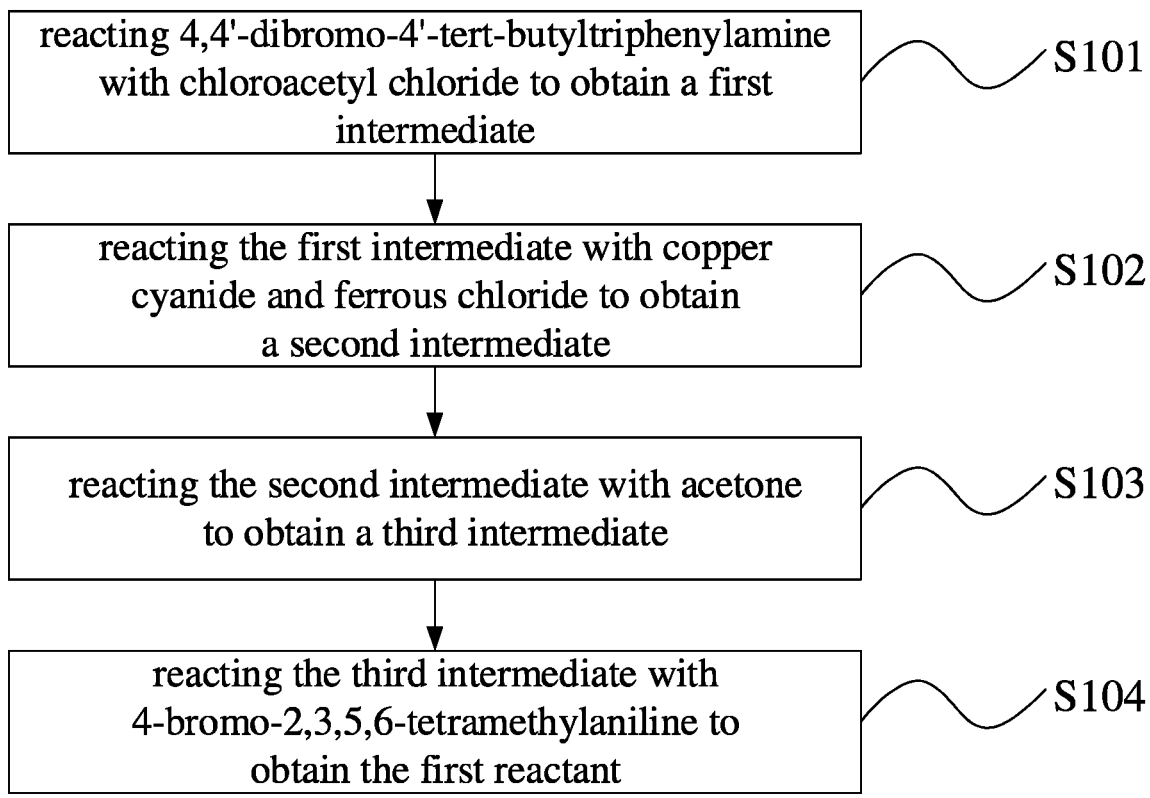
FIG. 2 is a flowchart of the manufacturing method of the first reactant according to the embodiment of the present disclosure.

As shown in FIG. 2, the manufacturing method for the first reactant includes:

a step S101 of reacting 4,4'-dibromo-4'-tert-butyltriphenylamine with chloroacetyl chloride to obtain a first intermediate, wherein a structural formula of the first intermediate is as shown in formula (C):

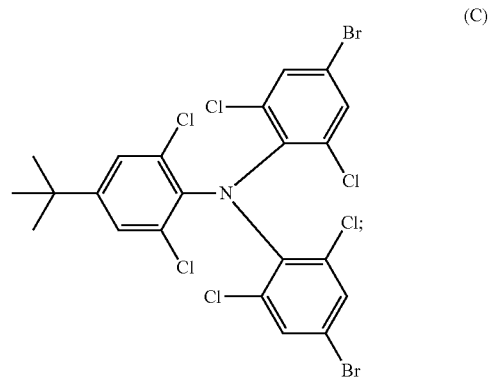 [SMILES: CC(C)(C)c1cc(Cl)c(N(c2c(Cl)cc(Br)cc2Cl)c2c(Cl)cc(Br)cc2Cl)c(Cl)c1]

a step S102 of reacting the first intermediate with copper cyanide and ferrous chloride to obtain a second intermediate, wherein a structural formula of the second intermediate is as shown in formula (D):

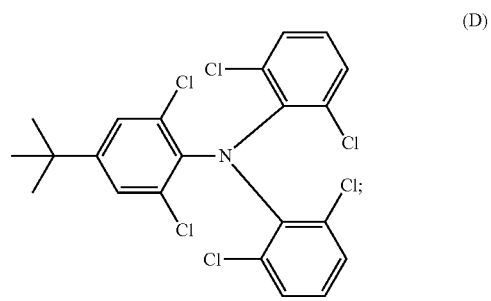 [SMILES: CC(C)(C)c1cc(Cl)c(N(c2c(Cl)cccc2Cl)c2c(Cl)cccc2Cl)c(Cl)c1]

a step S103 of reacting the second intermediate with acetone to obtain a third intermediate, wherein a structural formula of the third intermediate is as shown in formula (E):

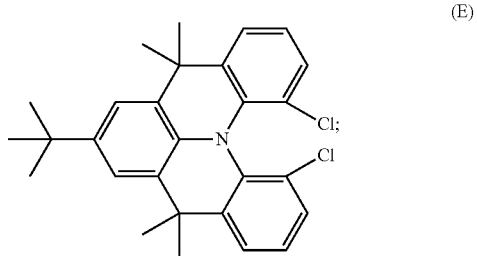 [SMILES: CC(C)(C)c1cc2c3c(c1)C(C)(C)c1cccc(Cl)c1N3c1c(Cl)cccc1C2(C)C]

and a step S104 of reacting the third intermediate with 4-bromo-2,3,5,6-tetramethylaniline to obtain the first reactant.

The synthesis process of the first reactant is as follows:

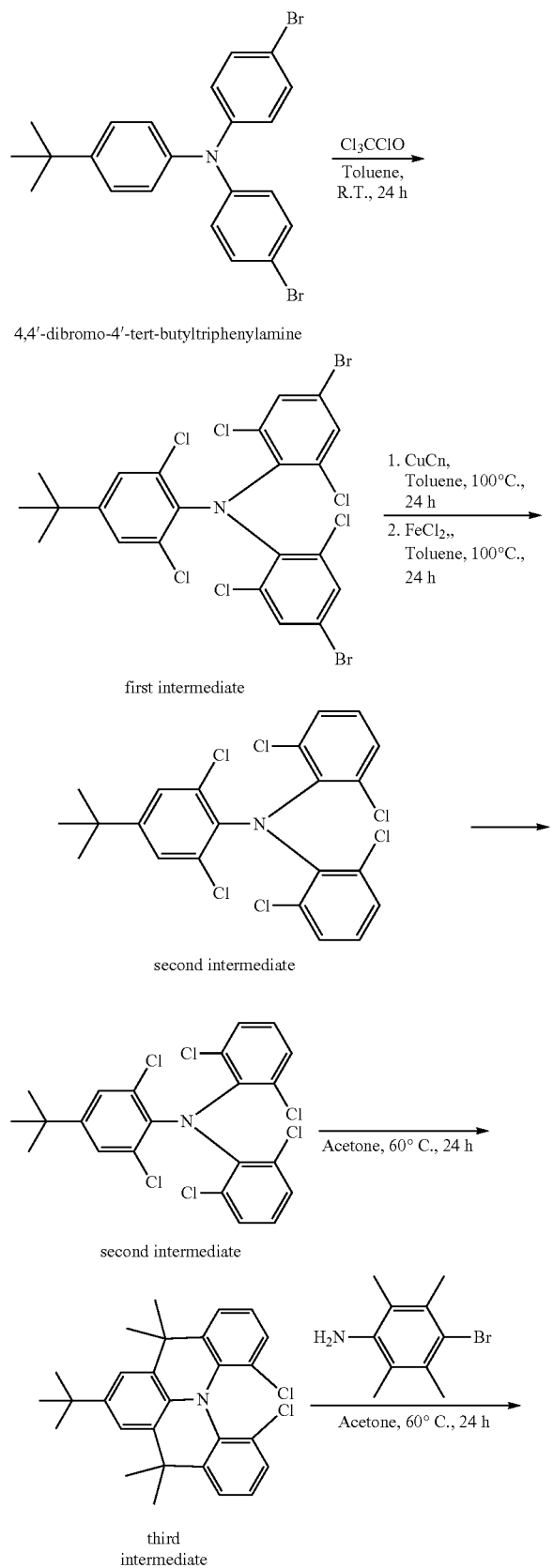

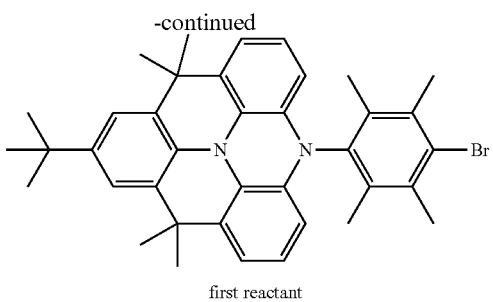

first reactant

Specifically, in the step S101, 4,4'-dibromo-4'-tert-butyl-triphenylamine (4.57 g, 10 mmol) and chloroacetyl chloride (16.7 g, 100 mmol) were added into a 250 mL two-neck flask. Then, in the presence of argon, 100 mL of dried and deoxidized toluene was introduced to react for 24 hours. The reacted solution was poured into 200 mL of ice water and extracted three times with dichloromethane. Then, organic phases were combined with the reacted solution, and rotary evaporation was performed to obtain silica gel. Isolation and purification were conducted by using column chromatography (dichloromethane:n-hexane, v:v, 2:1) to obtain white powder of 3.37 g. Yield: 51%. Mass spectrometry was performed on the white powder to obtain MS (EI) m/z: $[M]^+$: 660.73. the theoretical relative molecular weight of the first intermediate is 660.77.

In the step S102, the first intermediate (3.3 g, 5 mmol) and copper cyanide (0.54 g, 60 mmol) were added into a 250 mL two-neck flask. Then, in the presence of argon, 100 mL of dried and deoxidized toluene was introduced to react at 100° C. for 24 hours. Afterward, ferrous chloride (0.75 g, 60 mmol) was added. After cooling to room temperature, the reacted solution was poured into 200 mL of ice water and extracted three times with dichloromethane. Then, organic phases were combined with the reacted solution, and rotary evaporation was performed to obtain silica gel. Isloation and purification were conducted by using column chromatography (dichloromethane:n-hexane, v:v, 2:1) to obtain white powder of 2.01 g. Yield: 83%. Mass spectrometry was performed on the white powder. MS (EI) m/z: $[M]^+$: 504.88. The theoretical relative molecular weight of the second intermediate is 504.95.

In the step S103, the second intermediate (2.52 g, 5 mmol) was added into a 250 mL two-neck flask. Then, in the presence of argon, 100 mL of dried and deoxidized acetone was introduced to react at 60° C. for 24 hours. The reacted solution was poured into 200 mL of ice water and extracted three times with dichloromethane. Then, organic phases were combined with the reacted solution, and rotary evaporation was performed to obtain silica gel. Isolation and purification were conducted by using column chromatography (dichloromethane:n-hexane, v:v, 1:1) to obtain white powder of 1.70 g. Yield: 76%. MS (EI) m/z: $[M]^+$: 449.10. The theoretical relative molecular weight of the third intermediate is 449.17.

In the step S104, the third intermediate (2.25 g, 5 mmol) and 4-bromo-2,3,5,6-4-toluidine (1.39 g, 6 mmol) were added into a 250 mL two-neck flask. Then, in the presence of argon, 100 mL of dried and deoxidized acetone was introduced to react at 60° C. for 24 hours. The reacted solution was poured into 200 mL of ice water and extracted three times with dichloromethane. Then, organic phases were combined with the reacted solution, and rotary evaporation was performed to obtain silica gel. Isolation and purification were conducted by using column chromatography (dichloromethane:n-hexane, v:v, 1:1) to obtain white powder of 2.41 g. Yield: 80%. MS (EI) m/z: [M]⁺: 604.13. The theoretical relative molecular weight of the first reactant is 604.25.

Figure 3:
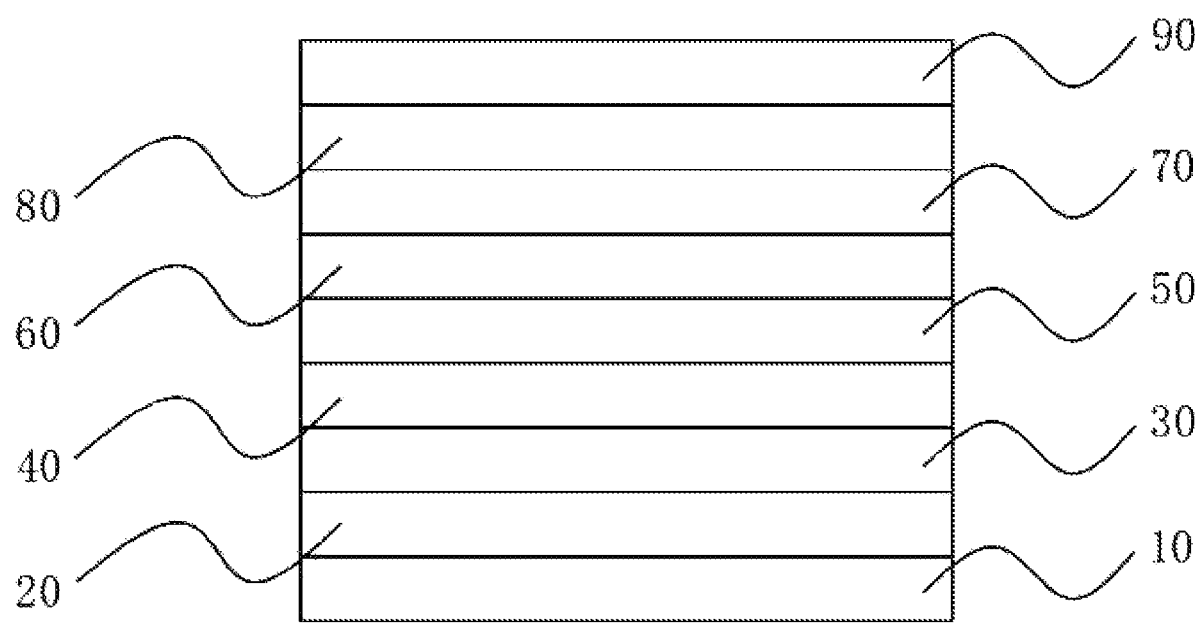
FIG. 3 is a schematic view of the structure of the organic electroluminescent device according to an embodiment of the present disclosure.

As shown in FIG. 3, the present embodiment further provides an organic electroluminescent device, comprising an anode 10, a hole injection layer 20, a hole transporting layer 30, an electron blocking layer 40, a light emitting layer 50, a hole blocking layer 60, an electron transporting layer 70, an electron injecting layer 80, and a cathode 90, all of which are sequentially stacked. The organic electroluminescent device further includes a light coupling output layer disposed on the cathode 90. Material of the hole transporting layer is prepared by the above method, and the material of the hole transport layer is the target compound 1.

The highest current efficiency of the hole transport layer in the embodiment is 38.9 cd/A, the chromatogram coordinates is (0.685, 0.290), and the maximum external quantum efficiency is 36.7%.

Embodiment 2

The first reactant (3.02 g, 5 mmol), phenoxazine (1.10 g, 6 mmol), palladium acetate (45 mg, 0.2 mmol), and tri-tert-butylphosphine tetrafluoroborate (0.17 g, 0.6 mmol) were added into a 250 mL two-neck flask. Then, NaOt-Bu (0.58 g, 6 mmol) was added into a glove box, and then in the presence of argon, 100 mL of dried and deoxidized toluene was introduced to react at 120° C. for 24 hours. After cooling to room temperature, the reacted solution was poured into 200 mL of ice water and extracted three times with dichloromethane. Then, organic phases were combined with the reacted solution, and rotary evaporation was performed to obtain silica gel. Isolation and purification were conducted by using column chromatography (dichloromethane:n-hexane, v:v, 1:5) to obtain a target compound 2. The target compound 2 is white powder of 2.6 g. Yield: 74%. MS (EI) m/z: [M]⁺: 707.32. The theoretical relative molecular weight of the target compound 2 is 707.37.

The synthesis process of the hole transporting material is as in the following formula (2).

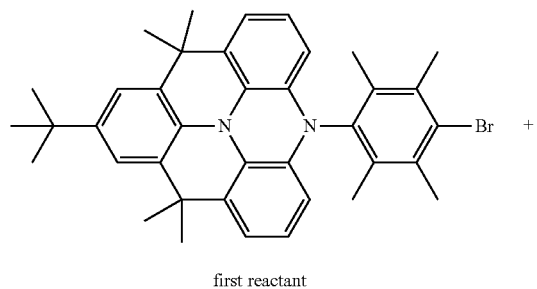

first reactant

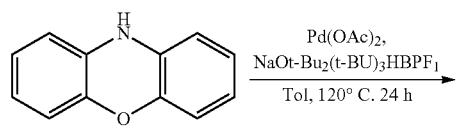

Pd(OAc)₂,
NaOt-Bu₂(t-BU)₃HBPF₁
———————————
Tol, 120° C. 24 h

-continued

[structure]

(2)

target compound 2

The target compound 2 has a highest occupied molecular orbital electrochemical energy level of −5.61 eV and a lowest unoccupied molecular orbital electrochemical energy level of −2.61 eV.

As shown in FIG. 3, the present embodiment further provides an organic electroluminescent device, comprising an anode 10, a hole injection layer 20, a hole transporting layer 30, an electron blocking layer 40, a light emitting layer 50, a hole blocking layer 60, an electron transporting layer 70, an electron injecting layer 80, and a cathode 90, all of which are sequentially stacked. The organic electroluminescent device further includes a light coupling output layer disposed on the cathode 90. Material of the hole transporting layer is prepared by the above method, and the material of the hole transport layer is the target compound 2.

The highest current efficiency of the hole transport layer in the embodiment is 35.2 cd/A, the chromatogram coordinates is (0.685, 0.290), and the maximum external quantum efficiency is 32.3%.

Embodiment 3

The first reactant (3.02 g, 5 mmol), 9,9′-dimethylacridine (1.26 g, 6 mmol), palladium acetate (45 mg, 0.2 mmol), and tri-tert-butylphosphine tetrafluoroborate (0.17 g, 0.6 mmol) were added into a 250 mL two-neck flask. Then, NaOt-Bu (0.58 g, 6 mmol) was added into a glove box, and then in the presence of argon, 100 mL of dried and deoxidized toluene was introduced to react at 120° C. for 24 hours. After cooling to room temperature, the reacted solution was poured into 200 mL of ice water and extracted three times with dichloromethane. Then, organic phases were combined with the reacted solution, and rotary evaporation was performed to obtain silica gel. Isolation and purification were conducted by using column chromatography (dichloromethane:n-hexane, v:v, 1:5) to obtain a target compound 3. The target compound 3 is white powder of 2.4 g. Yield: 65%. MS (EI) m/z: [M]⁺: 733.41. The theoretical relative molecular weight of the target compound 3 is 733.44.

The synthesis process of the hole transporting material is as in the following formula (3).

[structure]

first reactant

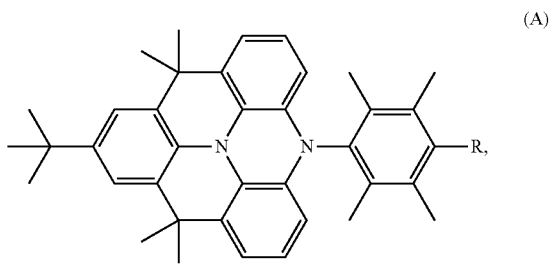

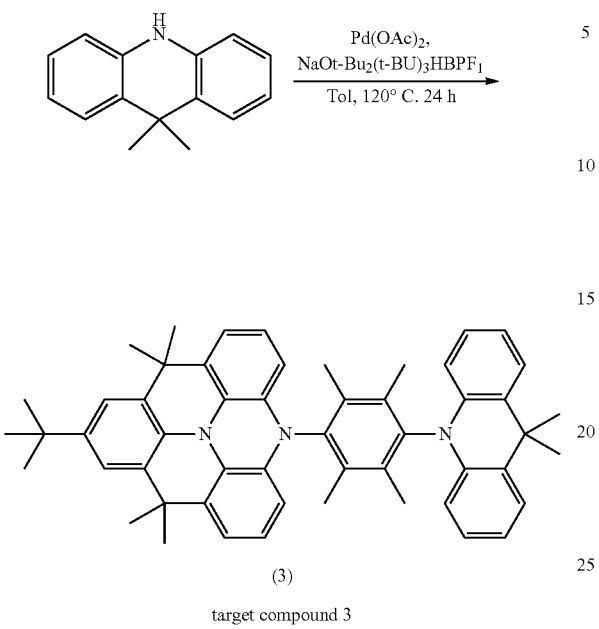

(3)

target compound 3

The target compound 3 has a highest occupied molecular orbital electrochemical energy level of −5.66 eV and a lowest unoccupied molecular orbital electrochemical energy level of −2.61 eV.

As shown in FIG. 3, the present embodiment further provides an organic electroluminescent device, comprising an anode 10, a hole injection layer 20, a hole transporting layer 30, an electron blocking layer 40, a light emitting layer 50, a hole blocking layer 60, an electron transporting layer 70, an electron injecting layer 80, and a cathode 90, all of which are sequentially stacked. The organic electroluminescent device further includes a light coupling output layer disposed on the cathode 90. Material of the hole transporting layer is prepared by the above method, and the material of the hole transport layer is the target compound 3.

The highest current efficiency of the hole transport layer in the embodiment is 36.8 cd/A, the chromatogram coordinates is (0.685, 0.290), and the maximum external quantum efficiency is 33.5%.

The beneficial effects: the hole transporting material is synthetized to have a suitable energy level and high mobility by using an acridine structure as a core with different functional groups, and an organic electroluminescent device based on the hole transporting material has high luminous efficiency.

In summary, although a few preferred embodiments of the present disclosure have been disclosed, the above preferred embodiments are not used for limiting this disclosure, and it will be understood by those of ordinary skill in the art that various changes in form and details may be made therein without departing from the spirit and scope of the present disclosure. The protection scope of the present disclosure is based on the scope of the appended claims.

The invention claimed is:

1. A hole transporting material, having a structural formula as shown in the following formula (A):

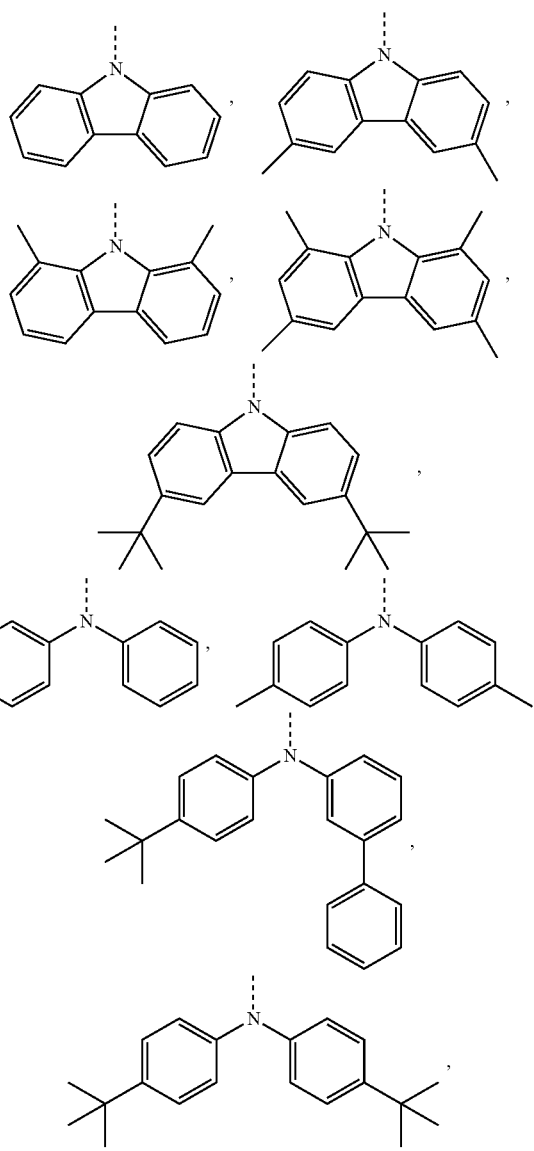

wherein R group is one of a carbazole group or a derivative group thereof, a diphenylamine group or a derivative group thereof, a phenoxazine group or a derivative group thereof, and an acridine group or a derivative group thereof.

2. The hole transporting material of claim 1, wherein the R group is one of the following structural formulas:

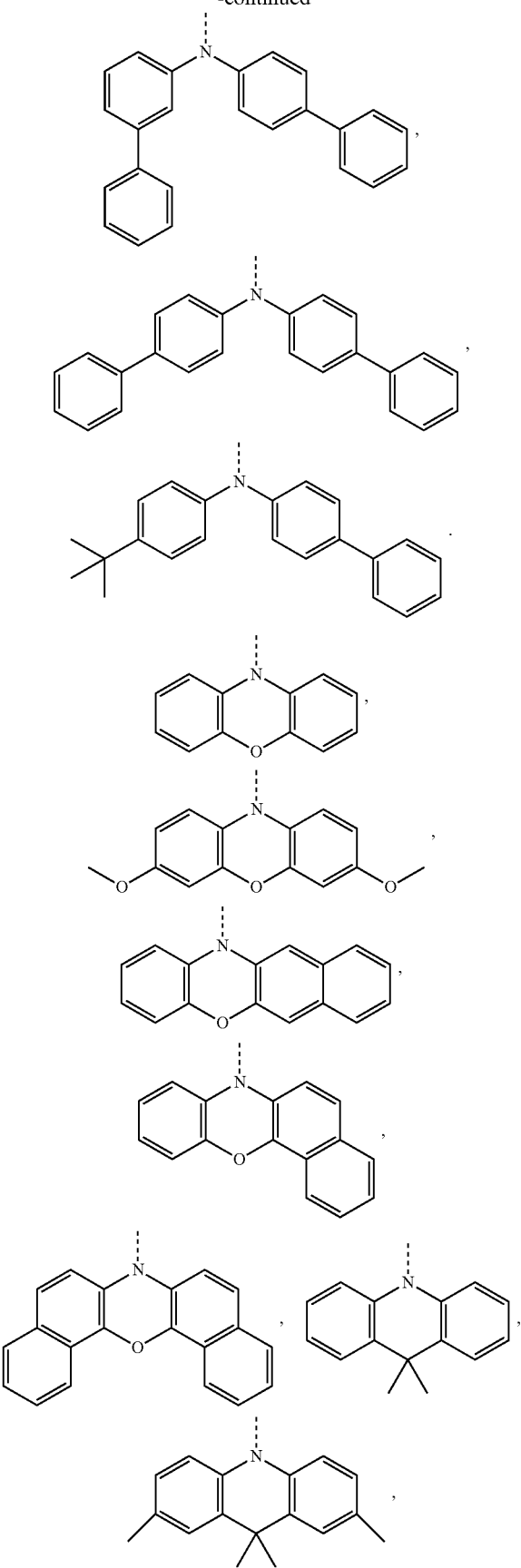

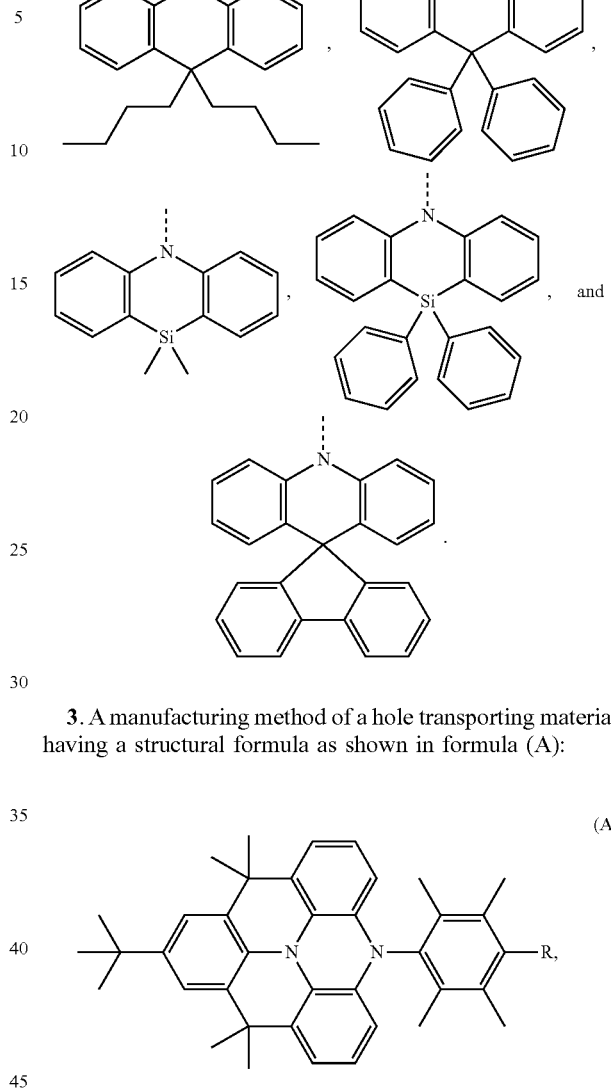

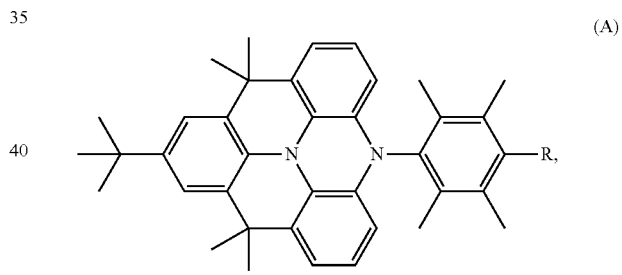

3. A manufacturing method of a hole transporting material having a structural formula as shown in formula (A):

(A)

wherein R group is one of a carbazole group or a derivative group thereof, a diphenylamine group or a derivative group thereof, a phenoxazine group or a derivative group thereof, and an acridine group or a derivative group thereof, the manufacturing method of the hole transporting material comprising:
a step S10 of mixing a first reactant, a second reactant, palladium acetate and tri-tert-butylphosphine tetrafluoroborate to obtain a mixed solution;
a step S20 of disposing the mixed solution in a glove box, adding sodium tert-butoxide and toluene into the mixed solution to react, and cooling to room temperature to obtain a reacted solution; and
a step S30 of extracting the reacted solution, combining organic phases obtained by extracting, and isolating and purifying the organic phases to obtain the hole transporting material.

4. The manufacturing method of claim 3, wherein the second reactant is one of carbazole or derivatives thereof, diphenylamine or derivatives thereof, phenoxazine or derivatives thereof, and acridine or derivatives thereof.

5. The manufacturing method of claim 4, wherein the second reactant is one of carbazole, phenoxazine and 9,9'-dimethylacridine.

6. The manufacturing method of claim 4, wherein a structural formula of the first reactant is as shown in formula (B):

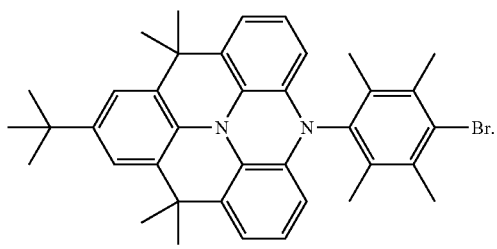

(B)

7. The manufacturing method of claim 6, wherein the first reactant is prepared by:

a step S101 of reacting 4,4'-dibromo-4'-tert-butyltriphenyl amine with chloroacetyl chloride to obtain a first intermediate, wherein a structural formula of the first intermediate is as shown in formula (C):

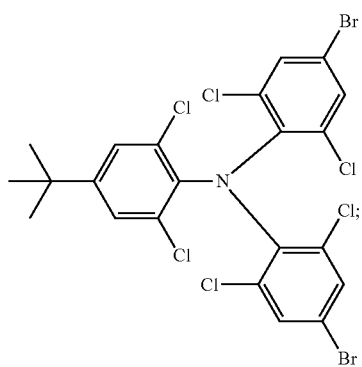

(C)

a step S102 of reacting the first intermediate with copper cyanide and ferrous chloride to obtain a second intermediate, wherein a structural formula of the second intermediate is as shown in formula (D):

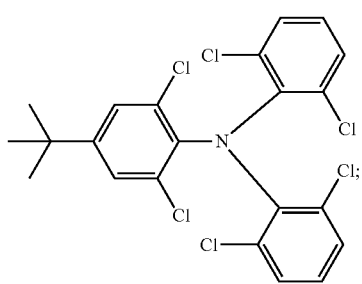

(D)

a step S103 of reacting the second intermediate with acetone to obtain a third intermediate, wherein a structural formula of the third intermediate is as shown in formula (E):

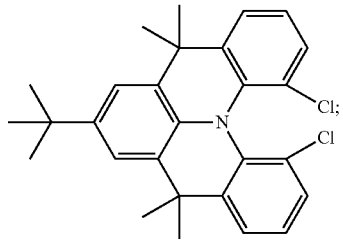

(E)

and a step S104 of reacting the third intermediate with 4-bromo-2,3,5,6-tetramethylaniline to obtain the first reactant.

8. The manufacturing method of claim 3, wherein in the step S20, reaction temperature is 120° C. and reaction time is 24 hours.

9. The manufacturing method of claim 3, wherein the step S30 comprises steps of:

pouring the reaction solution into ice water, and combining the organic phases obtained after extracting several times with dichloromethane; and performing rotary evaporation to the organic phases to obtain silica gel, and then isolating and purifying by using column chromatography to obtain the hole transporting material.

10. An organic electroluminescent device, comprising: a hole transporting material having a structural formula as shown in the following formula (A):

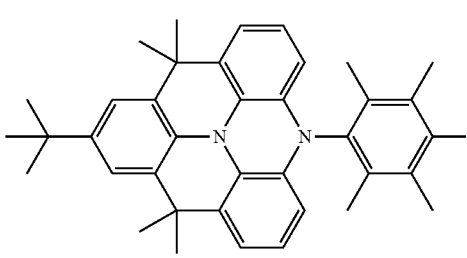

(A)

wherein R group is one of a carbazole group or a derivative group thereof, a diphenylamine group or a derivative group thereof, a phenoxazine group or a derivative group thereof, and an acridine group or a derivative group thereof.

11. The organic electroluminescent device of claim 10, wherein the R group is one of the following structural formulas:

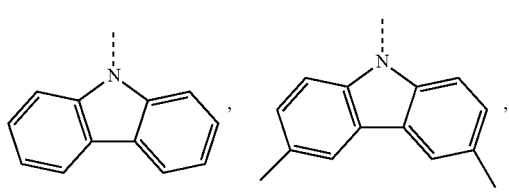

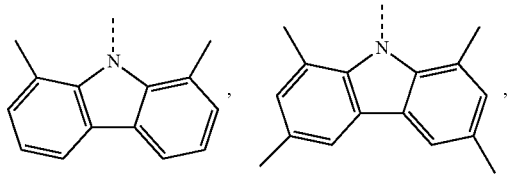
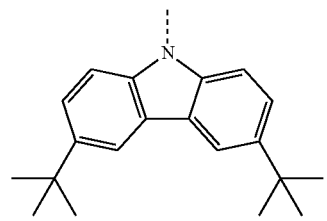
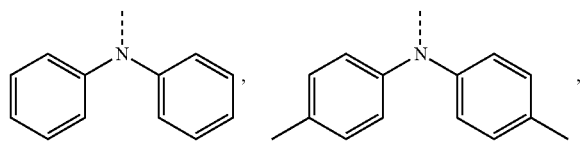
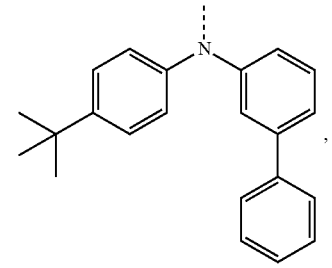
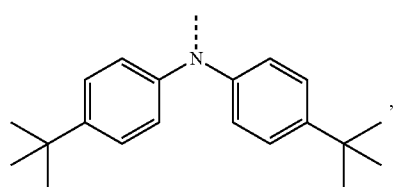
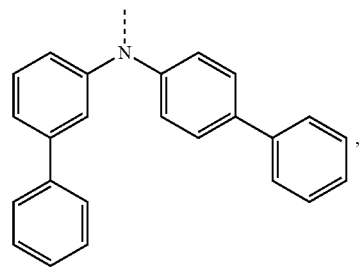
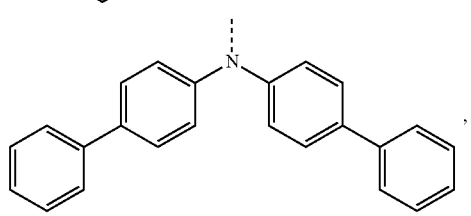
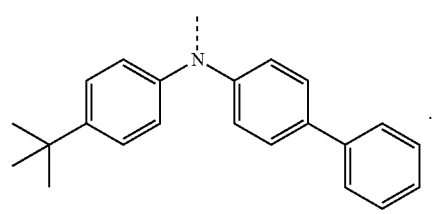
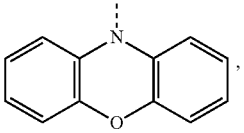
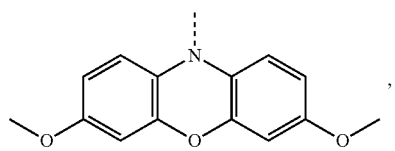
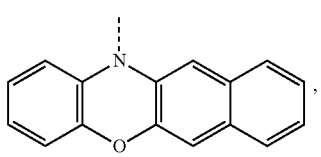
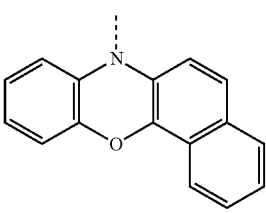
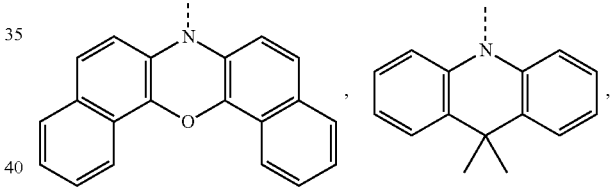
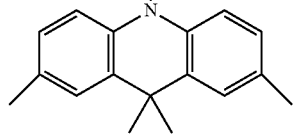
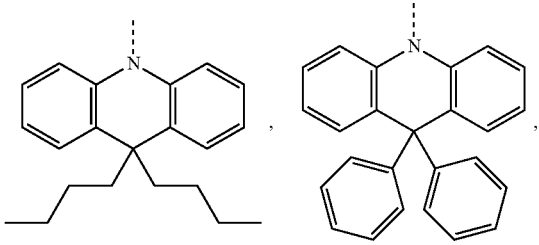
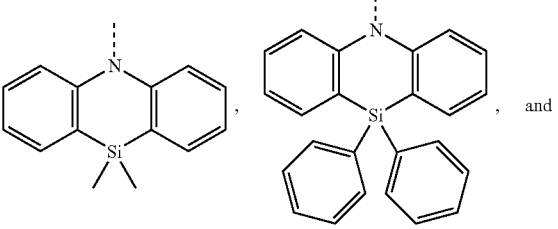, and -continued
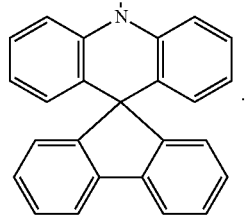
* * * * *